United States Patent
Planker

[19]
[11] Patent Number: 6,142,383
[45] Date of Patent: Nov. 7, 2000

[54] METHOD OF WATERLESS LARGE SCALE DISPERSION OF ESSENTIAL OILS AND APPARATUS THEREFOR

[75] Inventor: Timothy W. Planker, Cape Coral, Fla.

[73] Assignee: Hinsilblon Laboratories, Cape Coral, Fla.

[21] Appl. No.: 09/282,432

[22] Filed: Mar. 31, 1999

Related U.S. Application Data

[60] Provisional application No. 60/081,010, Apr. 8, 1998.

[51] Int. Cl.[7] ........................................................ B05B 7/26
[52] U.S. Cl. ............................... 239/8; 239/311; 239/317
[58] Field of Search ................................ 239/8, 302, 310, 239/311, 317; 422/4, 5, 124, 305, 306; 261/78.2, DIG. 26

[56] References Cited

U.S. PATENT DOCUMENTS

| | | |
|---|---|---|
| 3,442,602 | 5/1969 | Diehl . |
| 3,576,593 | 4/1971 | Cicirello . |
| 4,166,087 | 8/1979 | Cline et al. . |
| 4,268,285 | 5/1981 | Mason ................................. 422/124 X |
| 4,294,778 | 10/1981 | DeLuca ................................. 422/124 X |
| 4,780,253 | 10/1988 | Fukuhara et al. ................... 261/78.2 X |
| 5,370,829 | 12/1994 | Kunze .................................. 422/124 X |
| 5,480,591 | 1/1996 | Lagneaux et al. ................... 422/124 X |
| 5,725,833 | 3/1998 | Crafton . |
| 5,735,918 | 4/1998 | Barradas ............................. 422/124 X |

OTHER PUBLICATIONS

Harold J. Rafson, "Odor and VOC Control Handbook", McGraw–Hill, New York, Section 8.2, pp. 8.18–8.24.

*Primary Examiner*—Lesley D. Morris
*Attorney, Agent, or Firm*—Arent Fox Kintner Plotkin & Kahn, PLLC

[57] ABSTRACT

Waterless large scale dispersion method for essential oils which includes containing the liquid essential oil in a reservoir, simultaneously heating and blowing a gas over a surface of liquid essential oil in the reservoir to convert the oil to vapor, controlling the flow of gas by bypassing a portion of the gas around the reservoir, and distributing the vapor via one or more nozzles into a very large scale space. A constant speed regenerative blower is used to heat and blow air through the reservoir. A simple bypass valve controls the air flow through the reservoir.

19 Claims, 3 Drawing Sheets

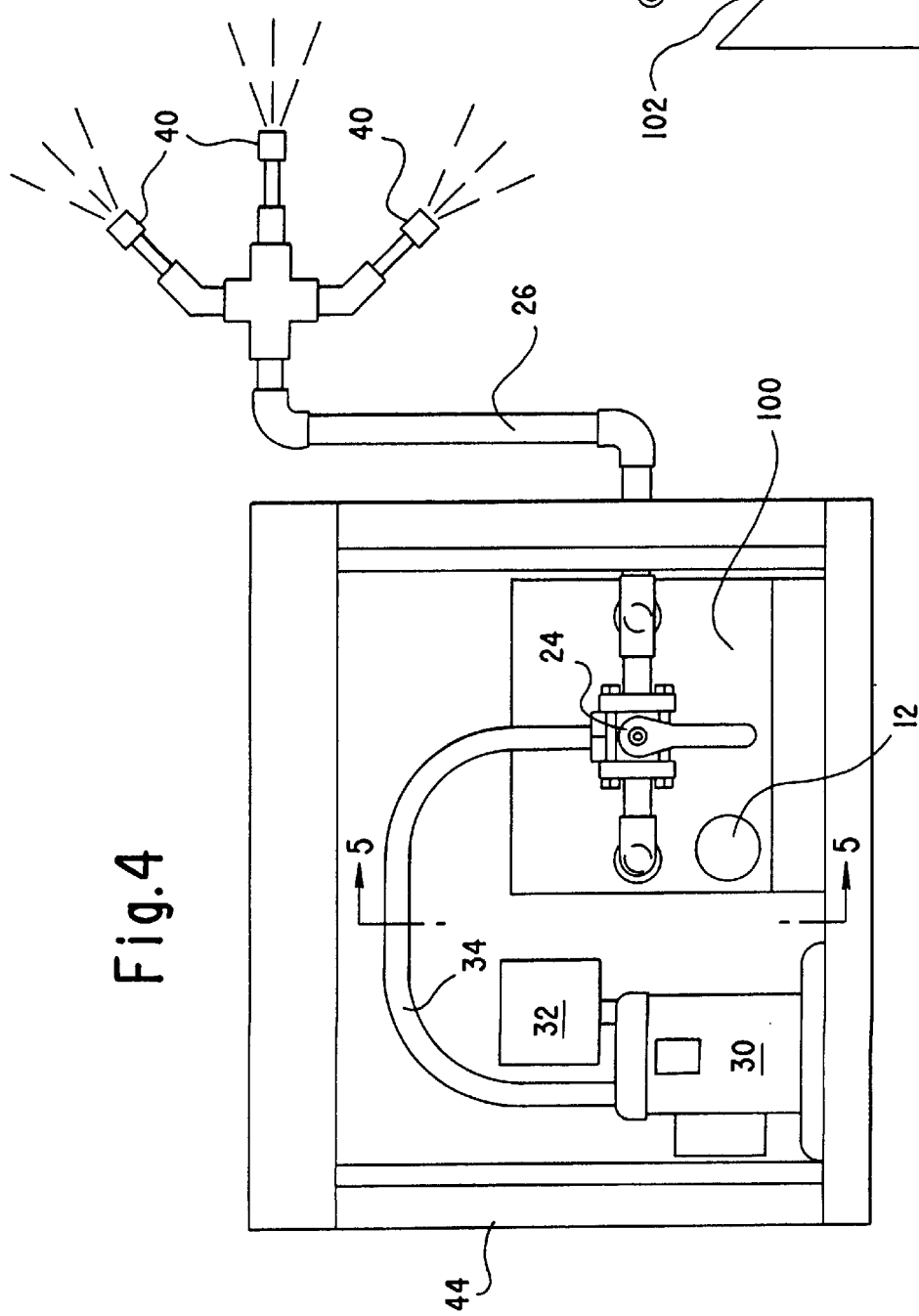
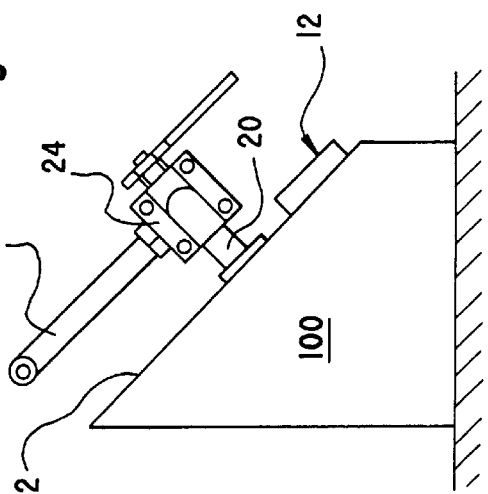

METHOD OF WATERLESS LARGE SCALE DISPERSION OF ESSENTIAL OILS AND APPARATUS THEREFOR

This application claims the benefit of U.S. Provisional Application No. 60/081,010, filed Apr. 8, 1998.

BACKGROUND OF THE INVENTION

The present invention relates to a method and apparatus for dispensing the aroma of essential oils into a very large scale space or volume without the need for water.

Essential oils are distilled or collected oils of naturally occurring substances.

Essential oils are liquids extracted from plant material by pressing, solvent extraction, or steam distillation. Generally, these have been known for many years. These organic, naturally-occurring essential oils are extracted from the seeds, bark, roots, leaves, flowers, wood, balsam, resin, and fruit of plants. The oils are then redistilled or rectified to remove any unwanted materials. Essential oils easily evaporate infusing the air without leaving an oily residue behind. Some examples are pine oil, oil of eucalytus, oil of peppermint, oil of basil, oil of orange, oil of rosemary, oil of cedarwood, and oil of spearmint. The smell of these oils can be pleasing to some people. An open container can be left standing and a faint amount of the aroma of the oils will spread. There is a difficulty in diffusing the aroma of the oils into a room to a larger degree since the boiling points of these oils is about 172° C.

Essential oils are extremely complex compositions consisting of hundreds of different organic compounds and trace elements. Organic compounds for many years were thought to only be made by living organisms containing a "vital force". In 1845, the German chemist Hermann Kolbe successfully synthesized acidic acid ending this organic "vital force" theory, yet the name organic compounds is still used. The following table lists the chemical families of the organic compounds in which essential oils are found.

Basic Chemistry: In general, essential oils consist of chemical compounds that have hydrogen, carbon and oxygen as their building blocks. These can be subdivided into two groups: the hydrocarbons, which are made up almost exclusively of terpenes (monoterpenes, sesquiterpenes and diterpenes); and the oxygenated compounds, mainly esters, aldehydes, ketones, alcohols, phenols and oxides; acids, lactones, sulphur and nitrogen compounds are sometimes also present.

Aldehydes: Citral, citronellal and neural are important aldehydes found notably in lemon-scented oils such as melissa, lemongrass, lemon verbena, lemon-scented eucalyptus, citronella, etc. Aldehydes in general have a sedative effect; citral has been found to have specifically antiseptic properties. Other aldehydes include benzaldehyde, cinnamic aldehyde, cuminic aldehyde and perillaldehyde.

Phenols: These tend to have a bactericidal and strongly stimulating effect, but can be skin irritants. Common phenols include eugenol (found in clove and West Indian bay), thymol (found in thyme), carvacrol (found in oregano and savory); methyl eugenol, methyl chavicol, anethole, safrole, myristicin and apiol among others.

Terpenes: Common terpene hydrocarbons include limonene (antiviral, found in 90 per cent of citrus oils) and pinene (antiseptic, found in high proportions in pine and turpentine oils); also camphene, cadinene, caryophyllene, cedrene, dipentene, phellandrene, terpinene, sabinene, and myrcene among others. Some sesquiterpenes, such as chamazulene and farnesol (both found in chamomile oil), have been the object of great interest recently because of their outstanding antiinflammatory and bactericidal properties.

Ketones: Some of the most common toxic constituents are ketones, such as thujone found in mugwort, tansy, sage and worm-wood; and pulegone found in pennyroyal and buchu but this does not mean that all ketones are dangerous. Non-toxic ketones include jasmone found in jasmine, and fenchone in fennel oil. Generally considered to ease congestion and aid the flow of mucus, ketones are often found in plants that are used for upper respiratory complaints, such as hyssop and sage. Other ketones include camphor, carvone, methone, methyl nonyl ketone and pinocamphone.

Oxides: By far the most important oxide in cineol (or eucalyptol), which stands virtually in a class of its own. It has an expectorant effect, well known as the principal constituent of eucalyptus oil. It is also found in a wide range of other oils, especially those of a camphoraceous nature such as rosemary, bay laurel, tea tree and cajeput. Other oxides include linalol oxide found in hyssop (decumbent variety), ascaridol, bisabolol oxide and bisabolone oxide.

Esters: Probably the most widespread group found in essential oils, which includes linalyl acetate (found in bergamot, clary sage and lavender), and geranyl acetate (found in sweet marjoram). They are characteristically fungicidal and sedative, often having a fruity aroma. Other esters include bornyl acetate, eugenyl acetate and lavendulyl acetate.

Alcohols: One of the most useful groups of compounds, tending to have good antiseptic and antiviral properties with an uplifting quality; they are also generally non-toxic. Some of the most common terpene alcohols include linalol (found in rosewood, lineloe and lavender), citronellol (found in rosewood, lineloe and lavender), citronellol (found in rose, lemon, eucalyptus and geranium) and geraniol (found in palmarosa); also borneol, methol, nerol, terpineol, farnesol, vetiverol, benzyl alcohol and cedrol among others.

Essential oils contain many constituents. The predominant components are terpenes and esters, but a large number of trace elements are also present. It is these trace elements that give the real essential oil its character and enhance its ability to blend with the other oils.

An example of this is Folded Orange Peel Oil. Orange Peel Oil is a concentrated product obtained by high vacuum distillation of the winterized peel oil of fresh oranges. The folding process removes much of the terpene hydrocarbon, d-limonene, while retaining the highly aromatic components. Clarified (or folded) oils have several times the potency of the original oil while maintaining the best odor modifying properties. The Valencia orange oil, for example, contains over 200 trace elements which have a synergistic or controlling effect on the desired potency. Trace elements exist in all natural essential oils at concentrations of less than one percent. Some trace elements exist at down to a few parts per trillion, e.g. ⅕th of a teaspoon (one gram) in 200 million gallons of water. It is these trace elements that provide the delicate, extremely complex nuances that give the natural oil its unique odor neutralizing quality.

A number of apparatuses are previously known for directly diffusing essential oils into a room. These include an integrally formed shallow open-top ceramic bowl having a cylindrical shell supporting it. The shell has an open front area and an integral base. Water is placed into the bowl, oils are spread upon the water, and a "tea" candle is lit and placed in through the open front area of the shell onto the base to heat the water and oils directly using the open flame.

A water buffered smokeless essential oil dispersing system is known in U.S. Pat. No. 5,725,833 using a charcoal briquette to heat water in a vessel resting thereon with the essential oils floating on top of the water.

These known systems are suitable for personal use for dispersing essential oils in a single room of reasonable size, but are entirely unsuitable when a large scale room or a very large scale room is contemplated. In this application, "large scale" means on the order of 1,000–10,000 square feet and "very large scale" means on the order of 10,000 square feet or larger. Also these systems are close to useless in the open air since the diffusion rate is so small and slow.

Other fogging systems are known for diffusing essential oils into the air require that the oil be diluted with water either before the dispersion or at the time of the dispersion. Such systems range from drum top foggers to massive size systems which are difficult to control and maintain. Many are expensive to build and to operate. All of these systems are subject to the problem that water is involved and must be supplied either a priori or simultaneously. Some difficulties are encountered with "rainout" and moisture condensation in the space where the dispersion is taking place. Such operations are almost impossible in winter.

SUMMARY OF THE INVENTION

The present invention is a method (direct vaporization) which vaporizes the essential oils directly into the air. In addition to very effectively dispensing the essential oils as desired, this system has the added benefit of being available at a very low capital cost and is easily maintained.

Direct vaporization fogging technology vaporizes the essential oils directly into the air. It has been designed for use with a super concentrated essential oil product and require no water. This process is recommended for outdoor dispensing especially in conditions of extreme cold where freezing can be a problem if a water based system were to be used or if for any other reason a system without water is preferred (such as in a closed arena or stadium). The direct vaporization process uses the heat generated by the blower blowing the air to evaporate the essential oils, creating a pleasant or at least desired odor vapor.

Many large indoor essential oil treatment applications are required only for a single event or for a short period. The significantly lower capital systems is ideal for these applications where a much more costly permanent system would not be fully utilized. Further, the portability of the apparatus becomes a major factor. Either the facilities owner desires equipment that can be easily stored when not needed or the road show owner desires equipment that is easy to stow and transport.

The present apparatus is especially useful in that it does not require a sophisticated electrical controller. The system can be manufactured with readily available component parts from local supply houses. The equipment can be operated and maintained with a minimal effort.

This system uses an evaporator to convert a super concentrated liquid essential oil to vapor. The vapor is then distributed via one or more nozzles. The direct vaporization system allows winter operation. The essential oils have a freezing point well below −100° F. so there is no concern of freezing. The direct vaporization system operates with no water.

BRIEF DESCRIPTION OF THE DRAWINGS

The above and other objects and the attendant advantages of the present invention will become readily apparent by reference to the following detailed description when considered in conjunction with the accompanying drawings wherein:

FIG. 4 is a front view of a second model differing from the first primarily in the design of the reservoir; and FIG. 5 is a side view of the reservoir of the second model.

DETAILED DESCRIPTION OF PREFERRED EMBODIMENTS

Figure 1:
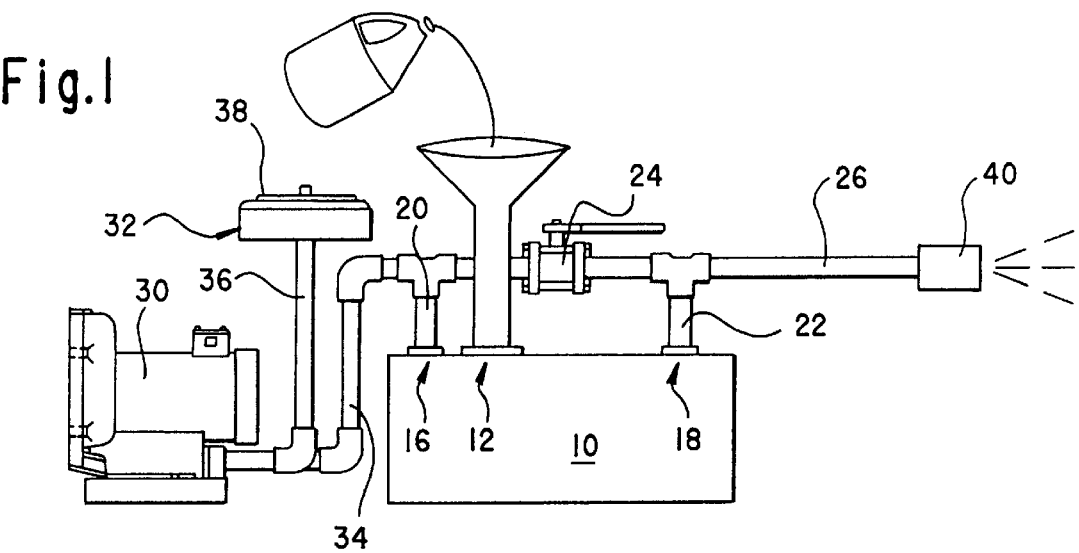
FIG. 1 is a front view of one model of the present invention.
Figure 2:
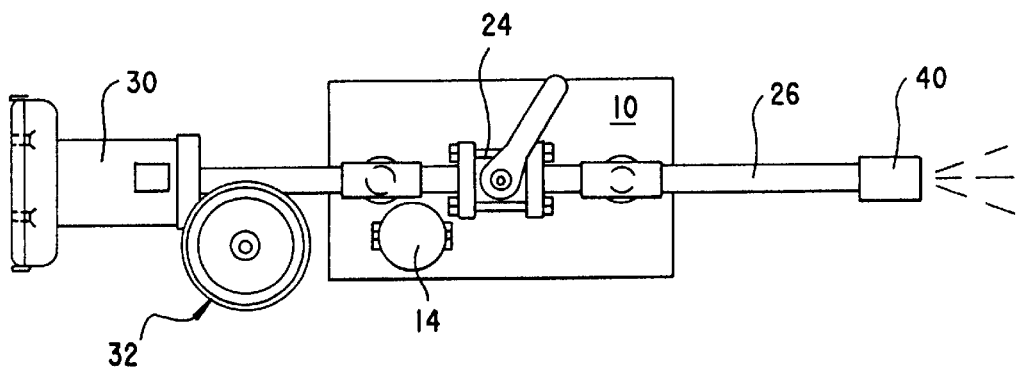
FIG. 2 is a top plan view of the same.

The equipment is essentially as shown in front view in FIG. 1 and in a top plan view in FIG. 2. In FIG. 1, the evaporator reservoir 10 is being manually filled with the essential oil to be dispensed. In FIG. 2, the reservoir 10 is closed. The reservoir 10 is basically a rectangular box with three openings 12, 16, 18. In one model, the reservoir is made of welded aluminum and has a 7 ½ gallon capacity. One of the openings 12 is the fill port which when in use is closed by a cam lever type port cap 14. The other two 16, 18 have pipes 20, 22 extending upwardly. The first and second pipes 20, 22 are joined to each other with a bypass valve 24. A regenerative air blower 30 is connected via a blower outlet pipe 34 to one pipe 20 while the other pipe 22 is extended via a vapor distribution pipe 26 to a nozzle 40 for dispensing the oil in a fog like manner.

Figure 3:
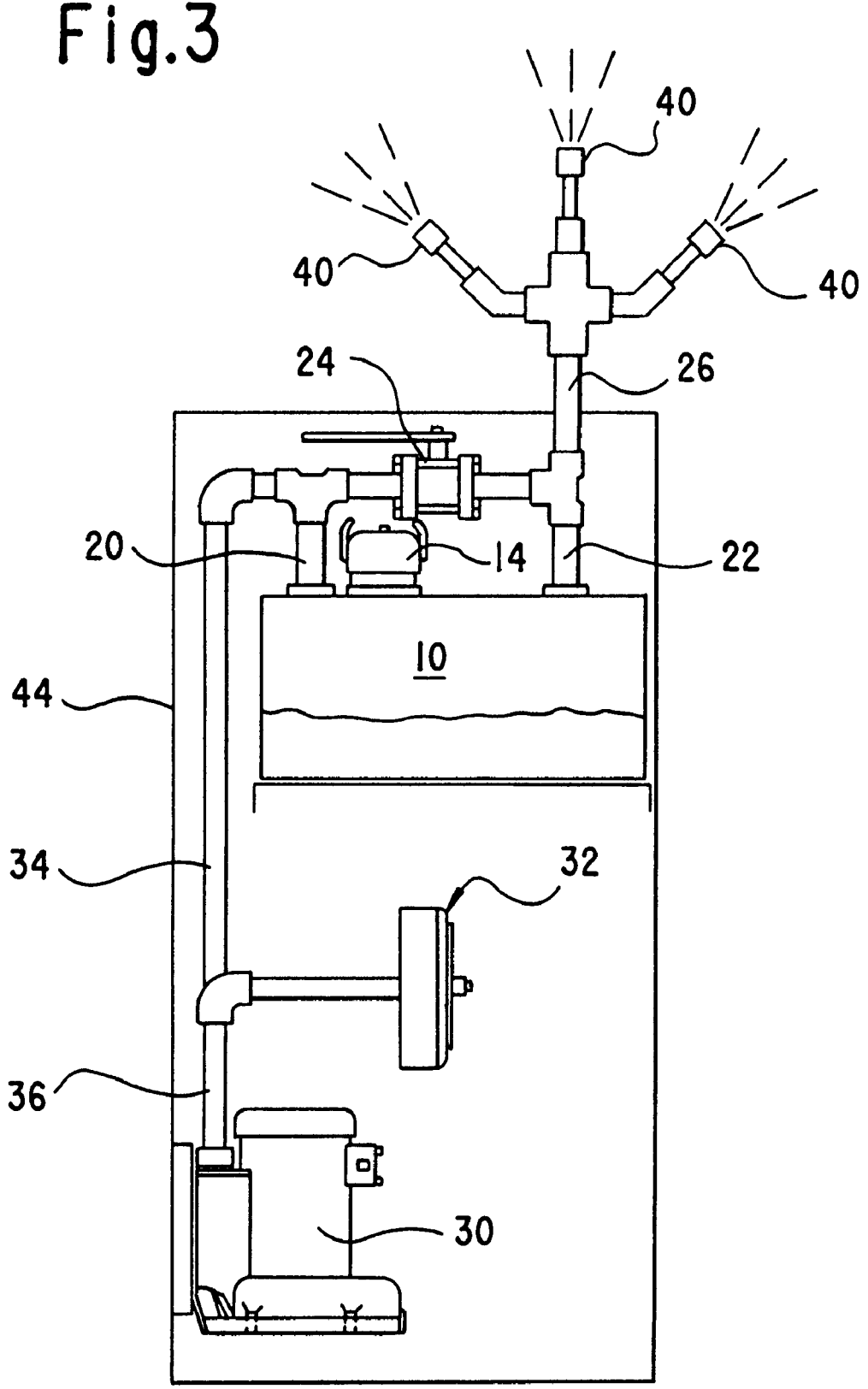
FIG. 3 is a front view of the first model in a self supported commercial cabinet.

FIG. 3 shows an alternative mounting for the equipment in which multiple nozzles 40 are provided and the apparatus is generally oriented in a vertical manner. The cam lever type fill port cap 14 is more clearly shown. The piping is preferably 2' Schedule 80 and can be polypropylene. The nozzles 40 are stock nozzles, such as those manufactured by Bete Fog Nozzle Co., which can have a nozzle orifice of ¼" and, for example, can be made of polypropylene. Standard pipe fittings and couplings are useable.

The motor for the regenerative air blower 30 can be a TEFC of stock sizes, such as, ½ horsepower (HP), ¾ HP, 1 HP, 3 HP, and 5 HP. Permanently sealed ball bearings are preferable. The larger the blower is, the more nozzles that can be used and a greater area covered. The number of nozzles that can be used in a given unit ranges from a single nozzle for the smallest unit to twenty nozzles for the 5 HP size. The blower 30 itself has a cast aluminum housing, impeller, and cover with the inlet and outlet muffling meeting or exceeding all appropriate OSHA noise standards. The intake air is filtered with an air filter 32 containing, for example, a standard replaceable, pleated paper filter cartridge. The air filter 32 is contained in a standard air filter cover 38 and is connected to the blower by inlet pipe 36. The regenerative air blower unit, reservoir, and extending pipe with nozzle can be easily mounted as a single unit in a housing 44. The orientation can be horizontal on a single bed or platform as shown in FIGS. 1 and 2 or can be vertical as shown in FIG. 3.

The outside air heated by the ordinary action of the regenerative blower is passed through the reservoir over the surface of the essential oils which have been poured in there. There is not believed to be any bubbling action and it is believed that the simple passage of the heated air over the oils evaporates a sufficient amount of the oils to achieve the desired effect. The heated air containing the evaporated oils then leaves the reservoir and is blown out the nozzle(s). The bypass valve regulates the amount of heated air that passes into the reservoir and thereby regulates the amount of the oils evaporated and dispensed out the nozzle(s). Since the flow of the heated air over the oils is controlled simply by the bypass valve, the motor and blower can be constant speed thereby reducing complexity of the system. To use the system, the equipment is moved to the desired location, the essential oils are poured into the reservoir, the fill port is closed and capped, and the blower is started with the bypass valve wide open. Thereafter, as desired, the bypass valve is closed off to the degree to produce the amount of vaporization of the oils for the occasion.

A difficulty in practice has been encountered with respect to the configuration as shown in FIG. 3. In order to move the unit around and place it where desired, the entire unit has been tilted to the rear, (to the right hand side of FIG. 3). If the unit is tilted too far, the essential oils in the reservoir can flow up the pipe 20 leading back to the blower and drain the oils into the blower. The next time the blower is started, it burns out. To avoid this problem and make a more compact unit, the reservoir has been redesigned as shown in FIGS. 4 and 5.

Reservoir 100, instead of being a simple rectangular box, has side walls shaped as irregular trapezoids with the top 102 being a slant surface relative to horizontal. The top 102 is provided as in the first model with the openings 12, 16, and 18 with the pipes 20 and 22 connected thereto. The opening 12 serves as the fill port and is provided with a cap (not shown). As is apparent to those of skill in the art, even if the device is tilted rearwardly in FIG. 4 (to the left in FIG. 5) there is sufficient capacity in the reservoir to prevent any of the oil from flowing through the pipe 20 and back to the blower 30. An additional advantage of the system configured as shown in FIG. 4 over that shown in FIG. 3 is the relative compactness thereof.

It is readily apparent that the above-described has the advantage of wide commercial utility. It should be understood that the specific form of the invention hereinabove described is intended to be representative only, as certain modifications within the scope of these teachings will be apparent to those skilled in the art.

Accordingly, reference should be made to the following claims in determining the full scope of the invention.

What I claim is:

1. A method of waterless large scale dispersion of essential oil comprising:

blowing a gas over a surface of liquid essential oil to convert the oil to vapor, and distributing the vapor via one or more nozzles into a very large scale space, wherein the gas is simultaneously heated and blown by a regenerative blower.

2. The method of claim 1 wherein the very large scale space is outdoors.

3. The method of claim 1 wherein the very large scale space is an indoor space.

4. The method of claim 1 further comprising heating the gas prior to the gas passing over the surface of the oil.

5. The method of claim 1 further comprising containing the essential oil in a reservoir, blowing the gas through the reservoir, and controlling the flow of gas by bypassing a portion of the gas around the reservoir.

6. The method of claim 1 wherein the gas is air.

7. A method of waterless large scale dispersion of essential oil comprising:

containing the liquid essential oil in a reservoir, simultaneously heating and blowing a gas by a regenerative blower over a surface of liquid essential oil in the reservoir to convert the oil to vapor, controlling the flow of gas by bypassing a portion of the gas around the reservoir, and distributing the vapor via one or more nozzles into a very large scale space.

8. The method of claim 7 wherein the very large scale space is outdoors.

9. A system for waterless large scale dispersion of essential oil comprising:

a reservoir having at least a first and a second opening, a first pipe connected to the first opening, a blower connected to the first pipe, a second pipe connected to the second opening, a bypass valve between the first and second pipes, a vapor distribution pipe connected to the second pipe, and a nozzle connected to the vapor distribution pipe.

10. The system of claim 9 wherein the reservoir is a rectangular box.

11. The system of claim 9 wherein the reservoir has side walls shaped as irregular trapezoids and a top formed as a slant surface relative to horizontal.

12. The system of claim 9 wherein the blower is a constant speed regenerative blower.

13. The system of claim 9 further comprising an air filter attached to an inlet of the blower.

14. The system of claim 9 further comprising a filler opening in the reservoir and a cap closing the filler opening.

15. The system of claim 9 having plural nozzles.

16. The system of claim 9 further comprising a housing containing the reservoir, the blower, the first and second pipes and the bypass valve and having the vapor distribution pipe extending therefrom.

17. The system of claim 9 wherein the first and second pipes, the vapor distribution pipe and the nozzle are made of a polymer.

18. A system for waterless large scale dispersion of essential oil comprising:

a reservoir having at least a first opening, a second opening and a filler opening, a cap closing the filler opening, a first pipe connected to the first opening, a constant speed regenerative blower connected to the first pipe, an air filter attached to an inlet of the blower, a second pipe connected to the second opening, a bypass valve between the first and second pipes, a vapor distribution pipe connected to the second pipe, plural nozzles connected to the vapor distribution pipe, and a housing containing the reservoir, the blower, the first and second pipes and the bypass valve and having the vapor distribution pipe extending therefrom.

19. The system of claim 18 wherein the first and second pipes, the vapor distribution pipe and the nozzles are made of a polymer.

* * * * *